United States Patent
Craciun et al.

(10) Patent No.: US 7,538,247 B2
(45) Date of Patent: May 26, 2009

(54) PREPARATION OF ACRYLIC ACID DERIVATIVES FROM α- OR β-HYDROXY CARBOXYLIC ACIDS

(75) Inventors: Liliana Craciun, Carmel, NY (US); Gerald P. Benn, Bradford (GB); John Dewing, Bradford (GB); George W. Schriver, Fort Lee, NJ (US); William J. Peer, Patterson, NJ (US); Bernd Siebenhaar, Kandern-Wollback (DE); Urs Siegrist, Frick (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 450 days.

(21) Appl. No.: 11/093,485

(22) Filed: Mar. 30, 2005

(65) Prior Publication Data

US 2005/0222458 A1    Oct. 6, 2005

Related U.S. Application Data

(60) Provisional application No. 60/558,839, filed on Apr. 2, 2004, provisional application No. 60/568,108, filed on May 4, 2004, provisional application No. 60/649,461, filed on Feb. 2, 2005.

(51) Int. Cl.
*C07C 231/00* (2006.01)

(52) U.S. Cl. .................................................. 564/141

(58) Field of Classification Search .................. None
See application file for complete search history.

(56) References Cited

U.S. PATENT DOCUMENTS

| | | | | |
|---|---|---|---|---|
| 2,464,768 A | 3/1949 | Redmon et al. | ............. | 260/486 |
| 2,466,501 A | 4/1949 | Steadman et al. | ........... | 260/486 |
| 2,469,701 A | 5/1949 | Redmon | ..................... | 260/526 |
| 2,548,155 A | 4/1951 | Gresham et al. | ............ | 260/561 |
| 2,649,438 A | 8/1953 | Bruson | ..................... | 260/85.5 |
| 3,639,466 A | 2/1972 | Leichtle | ..................... | 260/526 |
| 3,658,895 A | 4/1972 | Riemann et al. | ............ | 260/530 |
| 3,954,854 A | 5/1976 | Gehrmann et al. | .......... | 260/526 |
| 4,237,067 A | 12/1980 | Küster et al. | ................ | 564/205 |
| 4,464,539 A | 8/1984 | Hashimoto et al. | .......... | 560/212 |
| 5,075,493 A | 12/1991 | Shima et al. | ................ | 560/212 |
| 5,250,729 A | 10/1993 | Abe et al. | .................... | 562/599 |
| 5,268,507 A | 12/1993 | Brake | .......................... | 564/203 |
| 6,582,943 B1 | 6/2003 | Chauhan et al. | ............ | 435/146 |
| 7,001,969 B2 * | 2/2006 | Zhong et al. | ................ | 527/600 |
| 2002/0055650 A1 | 5/2002 | Hidaka et al. | ............... | 560/212 |

FOREIGN PATENT DOCUMENTS

| | | |
|---|---|---|
| EP | 0446446 | 9/1991 |
| ES | 8400383 | 1/1984 |
| GB | 648886 | 1/1951 |
| GB | 751750 | 7/1956 |
| GB | 2819735 | 11/1979 |
| WO | 03/051813 | 6/2003 |
| WO | 03/066815 | 8/2003 |
| WO | 03/082795 | 10/2003 |

OTHER PUBLICATIONS

Justus von Wislicenus, Liebig's Ann. Chem., vol. 166, (1873), pp. 1-64.
Justus von Wislicenus, Liebig's Ann. Chem., vol. 174, (1874), pp. 285-301.
English language abstract for ES 8400383 (1984).

* cited by examiner

*Primary Examiner*—Paul A Zucker
(74) *Attorney, Agent, or Firm*—Shiela A. Loggins

(57) ABSTRACT

The invention is directed to a process for the preparation of α,β-unsaturated acids, esters and amides from α- or β-hydroxycarboxylic acids or esters or precursors in high yields and high selectivity. The α,β-unsaturated acids or esters are optionally prepared in the presence of specific dehydration and/or esterification catalysts. The α,β-unsaturated amides or substituted amides are prepared optionally in the presence of a dehydration and/or amidation catalyst. The source of α- or β-hydroxycarboxylic acids or precusor is preferably from a renewable resource. The precursor is defined herein.

16 Claims, No Drawings

PREPARATION OF ACRYLIC ACID DERIVATIVES FROM α- OR β-HYDROXY CARBOXYLIC ACIDS

This application claims the benefit under 35 USC 119(e) of U.S. provisional application Nos. 60/558,839, filed Apr. 2, 2004, 60/568,108, filed May 4, 2004 and 60/649,461, filed Feb. 2, 2005.

The invention is directed to a process for the preparation of α,β-unsaturated acids, esters and amides from α or β-hydroxycarboxylic acids, polyhydroxyesters or other derivatives of α- or β-hydroxycarboxylic acids in high yields and high selectivity. The α,β-unsaturated acids and esters are optionally prepared, in the presence of dehydration and/or esterification catalysts. The α,β-unsaturated amides or substituted amides are optionally prepared in the presence of an amidation and/or dehydration catalyst. The source of α- or β-hydroxy-carboxylic acids may be from a synthetic or a renewable resource.

BACKGROUND

α- or β-hydroxycarboxylic acids are a highly useful class of compounds. They are bifunctional and therefore allow for multiple chemical transformations. The acid group can be converted to a variety of esters, amides, and substituted amides. The hydroxy group along with adjacent hydrogen can be eliminated thus leading to unsaturated compounds. The bifunctional nature of this class also allows polymerization to polyesters, oligomers, and cyclization to lactones or lactides.

Of particular interest is the preparation of commercially important α,β-unsaturated carboxylic acids and their derivatives such as esters, salts or amides of the acrylate and methacrylate families. (Meth)acrylic acid and its derivatives are used as monomers in the manufacture of polymers and copolymers. The formed polymers and copolymers have numerous applications for example in papermaking, solid/liquid separation processes, oil recovery and oil processing, mineral processing, municipal and industrial wastewater treatment, paper, surface coatings, personal care products, adhesives, sealants, absorbents, textile, non-wovens and as rheology modifiers.

Acrylic acid is manufactured by the oxidation of propylene. Acrylic esters are at present manufactured by the esterification of acrylic acid derived from propylene. Preparation of acrylic acid from propane is also known. The most common method of making methacrylic acid is from acetone cyanohydrin. Although propylene is readily available from fossil fuels it would be desirable to synthesize (meth)acrylic acids and esters from renewable resources at equivalent or lower cost.

Acrylamide is generally made by the catalytic hydration of acrylonitrile and substituted acrylamides are made by reacting acrylonitrile with olefins or alcohols under strongly acidic conditions. Other currently practiced processes for manufacture of acrylamides involve a lengthy three-step process starting with a Michael addition to the carbon-carbon double bond which is thermally reversed in the last deprotection step. Thus, a technically simple and economically attractive process from renewable resources for manufacture of (meth) acrylamides and substituted (meth)acrylamides in high yields would also be desirable.

The object of the present invention is to provide an inexpensive process using a starting material that could if desired be derived from wholly renewable resources for the production of these monomers. According to the present invention (meth)acrylic acid and esters are prepared in high yields and selectivity from α- or β-substituted hydroxycarboxylic acids, or precursors of the corresponding α- or β-substituted hydroxycarboxylic acids. The dehydration or dehydration/esterification of the α- or β-hydroxycarboxylic acid may take place in the presence of water and optionally may take place in the presence of a dehydration catalyst and/or esterification catalyst.

(Meth)acrylamides are prepared from α- or β-hydroxycarboxylic acids or derivatives where amidation and dehydration occur in a one or two-step process. Optionally an amidation and/or dehydration catalyst may be used for the reaction.

Furthermore, the (meth)acrylic acid, esters and amides may be made from α- or β-hydroxycarboxylic acids that are derived from biological sources. This could be in the form of α- or β-hydroxycarboxylic acids produced as part of a fermentation process or it may comprise polyhydroxyalkanoates such as polyhydroxypropionate or polyhydroxybutyrate that may be derived from biomass such as microbial cells or plant cells allowing for a most economical route from non-petroleum sources. The polyhydroxyalkanoates can be synthesized by the microbe or plant from sugars such as saccharides, agricultural materials and waste agricultural materials and other biomass.

PCT Application No. WO 03/051813 discusses the treatment of polyhydroxyalkanoates to form esters, amides and alkenoic acid derivatives.

U.S. Publication No. 20020055650 discloses the preparation of methacrylic acids and esters by treating hydroxyisobutyric acid or ester in the presence of an alcohol and solid catalyst.

U.S. Pat. No. 5,250,729 discloses a process for preparation of α,β-unsaturated acids or esters starting from an α- or β-hydroxycarboxylic acid ester. The reaction is carried out in the presence of an acidic dehydration catalyst.

U.S. Pat. No. 2,469,701 describes a process wherein hydracrylic acid is dehydrated at temperatures ranging from 130 to 190° C. in contact with an acid dehydration catalyst.

PCT Application No. WO03/82795 discloses the preparation of α,β-unsaturated carboxylic acid esters from β-hydroxycarboxylic acids or esters in the presence of an alcohol and dehydration catalyst.

U.S. Pat. No. 3,639,466 discloses a process for production of acrylic acid by heating a residue containing hydracrylic acid in the presence of an amine or tertiary phosphine.

U.S. Pat. No. 3,658,895 discloses reacting dilute solutions of acrylic acid with β-hydroxycarboxylic acid in the presence of an acid to form a polyester that is heated to form acrylic acid.

Spanish Patent Application No. ES 515891 discloses preparation of α,β-unsaturated carboxylic acids and/or their esters by dehydration of an α-hydroxycarboxylic acid or its ester in the presence of a solvent, a polymerization inhibitor, and a carrier gas with the aid of Group II, IIIA, IVB, and/or VIII metal sulfate and/or phosphate as catalyst.

German Application No. 3141173 discloses the preparation of α,β-unsaturated acids or their esters by contacting an α-hydroxycarboxamide $R_1R_2C(OH)CONH_2$ with a solid catalyst, alone or together with $H_2O$, or together with $H_2O$ and an aliphatic alcohol, or together with an aliphatic alcohol.

U.S. Pat. No. 3,954,854 discloses recovery of monomeric acrylic acid from a processed crude acrylic acid residue. The residue contains β-acryloxyloxypropionic acid, β-acetoxypropionic acid, hydracrylic acid, dihydracrylic acid and polymeric hydracrylic acid. This residue is treated with a cleavage catalyst at pressure of less than 1 atmosphere and heating to a temperature of 150 to 215° C.

U.S. Pat. No. 2,464,768 describes the preparation of low molecular weight acrylate esters by passing solutions of anhydrous β-hydroxypropionic acid in an excess of alcohol into a mixture of strong acid and copper powder at 130 to 170° C. and distilling out the acrylate ester and water.

European application No. 1,186,592 describes the production of methacryates by passage of solutions of α-hydroxyisobutric acid and an alcohol over a catalyst bed at elevated temperature.

U.S. Pat. No. 2,466,501 describes the preparation of α,β-unsaturated monocarboxylic acid esters by mixing propiolactone and an alcohol passed over an activated carbon catalyst to yield an acrylate ester.

Wislicenus, Justus von Liebig's Ann. Chem, 166, (1873), 1-64 and Wislicenus, Justus von Liebig's Ann Chem, 174, (1874), 285-301 describe the conversion of β-hydroxypropionic acid to acrylic acid. The conversion is achieved via distillation over lead or silver salts to form acrylic acid.

U.S. Pat. No. 2,649,438 describes the formation of acrylamides from β-propiolactone by treatment of the lactone with an amine followed by thermal dehydration. No details are given for this transformation.

Great Britain Publication No. 648,886 describes preparation of unsaturated substituted amides by reacting the β-propiolactone with primary or secondary amines, followed by heating and dehydration to form the substituted acrylamide.

U.S. Pat. No. 4,237,067 discloses a process for manufacture of α,β-unsaturated amides and substituted amides. The starting material is the β-hydroxycarboxylic acid amide. The elimination step requires the presence of an acid or base.

U.S. Pat. No. 5,268,507 describes preparation of amide derivatives of hydroxy acids.

German Application No. 2,819,735 describes the preparation of α,β-unsaturated N-substituted acid amides by heating the appropriate saturated β-hydroxyamide with the appropriate amine, followed by dehydration.

U.S. Pat. No. 2,548,155 describes the formation of hydracrylamide derivatives by treating β-propiolactone with substituted amines.

There is still a need for a process that allows for an efficient, mild and simple preparation of (meth)acrylic acid and its derivatives such as esters, salts and amides prepared from α- or β-hydroxycarboxylic acids or polymers, oligomers, lactides or lactones formed from α- or β-hydroxycarboxylic acids that are optionally derived from renewable resources such as biomass. A simple process is needed whereby the dehydration can be efficiently and effectively carried out in the presence of water under simple, mild reaction conditions. It is further desirable that the ester, acid or amide preparation takes place within the same reactor and virtually no by-products or significant amounts of hazardous waste materials are produced as a result of the reaction.

SUMMARY OF THE INVENTION

According to the present invention α,β-unsaturated acids and their derivatives are prepared by heating and dehydrating the appropriate α or β-hydroxycarboxylic acid or hydrolyzing and dehydrating the appropriate polymer, oligomers, lactides or lactones of the α- or β-hydroxycarboxylic acids optionally in the presence of a catalyst that could be oxides of Silane, Titanium or Aluminum or other suitable reaction catalysts. The α- or β-hydroxycarboxylic acids or the formed α,β-unsaturated acids from the dehydration reaction can be esterified using a suitable catalyst such as an aluminosilicate.

The (meth)acrylic acid or ester may be recovered by distillation or if the reaction takes place in the vapor phase, the product may be collected by condensation. The present invention also encompasses the preparation of α,β-unsaturated amides, α,β-unsaturated N-substituted amides and α,β-unsaturated N, N-disubstituted amides by heating the appropriate α- or β-hydroxycarboxylic acid, α- or β-hydroxycarboxylic ester, α- or β-hydroxycarboxylic salt, or their polymeric (polyester), oligomer, lactide or lactone precursors with an amine to amidate, followed by or simultaneously with dehydration. When dehydration is complete, the (meth)acrylamide or substituted (meth)acrylamide may be recovered by distillation, or if the reaction takes place in the vapor phase, the product may be collected by condensation.

Accordingly the invention encompasses, a process for preparing an α,β-unsaturated acid which comprises a) providing an aqueous solution comprising at least one of
   an α- or β-hydroxycarboxylic acid or salt thereof;
   a polyester, oligomer, lactide or lactone derivative of the α or β-hydroxycarboxylic acid;
   or
   an α- or β-hydroxycarboxylic acid derived from microbial or plant cells that contains or produces α- or β-hydroxycarboxylic acids, polyesters of α- or β-hydroxycarboxylic acids or other derivatives capable of being converted into an α- or β-hydroxycarboxylic acid, and b) heating the aqueous solution,
   optionally in the presence of a suitable dehydration catalyst.

It has also been discovered that the α,β-unsaturated acid can be formed by heating the α- or β-hydroxycarboxylic or precursor in the absence of catalyst.

Precursor for the purposes of the invention means
   a polyester, oligomer, lactide or lactone derivative of the α- or β-hydroxycarboxylic acid;
   or
   an α- or β-hydroxycarboxylic acid derived from microbial or plant cells that contains or produces α- or β-hydroxycarboxylic acids, polyesters of α- or β-hydroxycarboxylic acids or other derivative capable of being converted into an α- or β-hydroxycarboxylic acid.

Furthermore the invention encompasses, a process for preparing α,β-unsaturated carboxylic acid esters comprising a) providing an aqueous solution comprising at least one of
   an α- or β-hydroxycarboxylic acid or salt thereof;
   a polyester, oligomer, lactide or lactone derivative of α- or β-hydroxycarboxylic acid;
   or
   an α- or β-hydroxycarboxylic acid derived from a microbial or plant cells that contains or produces α- or α-hydroxycarboxylic acids, polyesters of α- or β-hydroxycarboxylic acids or other derivatives capable of being converted into an α- or β-hydroxycarboxylic acid, and b) heating the aqueous solution optionally in the presence of a catalyst, and step b) is carried out in the presence of an alcohol.

The catalyst may be a dehydration and/or an esterification catalyst.

Surprisingly it has been discovered that dehydration and esterification can take place using one catalyst only.

Accordingly, the invention encompasses a process for preparing α,β-unsaturated carboxylic acid esters comprising a) providing an aqueous solution comprising at least one of
an α- or β-hydroxycarboxylic acid or salt;
a polyester, oligomer, lactide or lactone derivative of the α- or
β-hydroxycarboxylic acid;
or
an α- or β-hydroxycarboxylic acid derived from a microbial or plant cells that contains or produces α- or β-hydroxycarboxylic acids, polyesters of α- or β-hydroxycarboxylic acids or other derivatives capable of being converted into an α- or β-hydroxycarboxylic acid,
and
b) heating the aqueous solution,
in the presence of a catalyst,
wherein step b) is carried out in the presence of an alcohol and the catalyst is an aluminosilicate.

Preferably the aluminosilicate is a zeolite.

Also the invention includes, a process for preparing an α,β-unsaturated amide, α,β-unsaturated N-substituted amide or α,β-unsaturated N,N-disubstituted amide comprising a) forming an aqueous solution comprising a compound from at least one of
an α or β-hydroxycarboxylic acid or salt;
an α- or β-hydroxycarboxylic ester;
a polyester, oligomer, lactide or lactone derivative of the α- or β-hydroxycarboxylic acid;
or
an α- or β-hydroxycarboxylic acid derived from a microbial or plant cells that contains or produces α- or β-hydroxycarboxylic acids, polyesters of α- or β-hydroxycarboxylic acids or other derivatives capable of being converted into an α- or β-hydroxycarboxylic acid,
and
b) heating the aqueous solution of a) in the presence of an amine or an amine salt of the α- or β-hydroxycarboxylic acid,
optionally in the presence of an amidation and/or dehydration catalyst.

The amine or amine salt is selected from the group consisting of ammonia, primary amines and secondary amines.

Another embodiment of the invention is a process for preparing α,β-unsaturated amides, α,β-unsaturated N-substituted amides or α,β-unsaturated N,N-disubstituted amides from a polyester of a α- or β-hydroxycarboxylic acid, or lactides thereof.

Additionally the invention includes, a process for preparing an α,β-unsaturated amide or α,β-unsaturated N-substituted amide comprising a) forming an aqueous solution comprising an α- or β-hydroxycarboxylic acid, an α- or β-hydroxycarboxylic esters or α- or β-hydroxycarboxylic acid salts, b) polymerizing to form a polyester, oligomer or cyclizing to form a cyclic lactide,
and a) heating the formed polyester or cyclic lactide of b) in the presence of an amine, optionally in the presence of an amidation and/or dehydration catalyst.

The aqueous solution comprising the α- or β-hydroxycarboxylic acid or precursor may optionally be derived from a fermentation process from sugars, or from a fermentation process that comprises biomass that may be microbial or plant cells that contains or produces α- or β-hydroxycarboxylic acids, polyesters of α- or β-hydroxycarboxylic acids or other precursor derivatives capable of being converted into an α- or β-hydroxycarboxylic acid.

DETAILED DESCRIPTION OF THE INVENTION

Aqueous solutions of β-hydroxycarboxylic acid can be dehydrated to (meth)acrylic acid or simultaneously dehydrated and esterified in the presence of an alcohol either by passing them in the vapor phase through a heated reactor containing catalytic packing or by carrying out the reaction in the liquid phase with the catalyst.

The α,β-unsaturated carboxylic acid or ester formed by the process of the invention is a compound of formula (I)

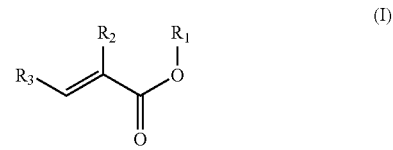

wherein $R_1$ is H, $C_1$-$C_8$ alkyl, $R_2$ is H or $C_1$-$C_4$ alkyl, and $R_3$ is H, methyl or ethyl.

$C_1$-$C_4$ alkyl can be a branched or unbranched carbon radical, for example, methyl, ethyl, propyl, isopropyl, n-butyl, tert-butyl, sec-butyl and isobutyl.

$C_1$-$C_8$ alkyl for the purposes of the invention can be a branched or unbranched alkyl radical, for example, methyl, ethyl, isopropyl, n-propyl, n-butyl, isobutyl, sec-butyl, 2-ethylbutyl, 1,3-dimethylbutyl, tert-butyl, isopentyl, 1-methylpentyl, n-pentyl, n-hexyl, 1-methylhexyl, 2-ethylhexyl and isoheptyl.

Preferably the α,β-unsaturated carboxylic acid made by the process is acrylic acid, methacrylic acid or crotonic acid.

The starting α- or β-hydroxycarboxylic acid or precursor may be an α- or β-hydroxycarboxylic acid such as 3-hydroxypropionic acid, lactic acid, 3-hydroxybutyric acid, 3-hydroxy-2-methylpropionic acid or 2-hydroxy-2-methylpropionic acid.

Preferably the α- or β-hydroxycarboxylic acid is a β-hydroxycarboxylic acid. Most preferably the β-hydroxycarboxylic acid is 3-hydroxypropionic acid, 3-hydroxy-2-methylpropionic acid, or 3-hydroxybutyric acid.

As the α- or β-hydroxycarboxylic acid is bifunctional, it may form polyesters, oligomers, lactones and lactides. Therefore the precursor for the purposes of the invention is defined as a polyester, oligomer, lactide or lactone derivative of the α- or β-hydroxycarboxylic acid. Alternatively the precursor is also defined as an α- or β-hydroxycarboxylic acid derived from a microbial or plant cells that contains or produces α- or β-hydroxycarboxylic acids, polyesters of α- or β-hydroxycarboxylic acids or other precursor derivatives capable of being converted into an a or β-hydroxycarboxylic acid.

These precursors may be derived from a fermentation process from sugars, or from a fermentation process that comprises biomass.

The α- or β-hydroxycarboxylic acid resource or precursor is preferentially an aqueous solution or fermentation broth containing the hydroxycarboxylic acid.

The concentration of the solution may vary from very low to high concentrations of the hydroxycarboxylic acid or precursor. For example, concentrations may vary from 10 to 90% based on the total weight of the solution. Preferably, concentrations of about 20 to 85% based on the total weight of the solution can be used as the starting material in the present invention.

An aqueous solution for the purposes of the invention, means substantial amounts of water are present in the starting material. For example, amounts greater than trace amounts or greater than the amount of water resulting from the dehydration reaction are present in the starting material.

Water in the aqueous solution will preferably be present in amounts greater than 1% and more preferably in amounts greater than 3% and most preferably in amounts greater than 10%.

An aqueous solution of the β-hydroxycarboxylic acid can be dehydrated to an α,β-unsaturated carboxylic acid by passing the solution in the vapor phase through a heated reactor optionally containing a catalytic packing.

The catalytic packing may function as a dehydration catalyst and may comprise metal oxides and/or aluminosilicates, prefereably metal oxides and/or zeolites. The metal oxide is selected from the group consisting of aluminum, silane or titanium oxides. Preferentially, the metal oxides are $\gamma$-$Al_2O_3$, $SiO_2$, $TiO_2$.

The dehydration catalyst is especially a high surface area $\gamma$-$Al_2O_3$ or a high surface area silica wherein the silica is substantially $SiO_2$. Substantially $SiO_2$ means for the purposes of the invention that the silica is not treated with strong acids such as $H_3PO_4$, $CuSO_4$, $NaH_2PO_4$ or $H_2SO_4$. The silica also does not serve as a support for a metal catalyst but is substantially $SiO_2$ Treated $SiO_2$ usually requires that the $SiO_2$ be impregnated with acid then calcined. Thus, the untreated $SiO_2$ offers the advantage of little or no pre-conditioning.

The most preferred dehydration catalyst is a high surface area $\gamma$-$Al_2O_3$ or a zeolite.

Thus the heated surface may be $Al_2O_3$, $SiO_2$, $TiO_2$ or an aluminosilicate.

High surface area for the purposes of the invention means a surface of about 100 $m^2$/g to about 500 $m^2$/g. Preferably, the surface area is at least about 125 $m^2$/g and especially at least about 150 $m^2$/g.

The dehydration of the α- or β-hydroxycarboxylic acid or precursor may also take place in the absence of a dehydration catalyst. For example, the reaction may be run in the vapor phase in the presence of an inert packing such as glass, ceramic, a resin, porcelain, plastic, metallic or brick dust packing and still form the α,β-unsaturated carboxylic acid in good yields and purity. This is especially surprising as the starting material is aqueous.

It has surprisingly been found that an aluminosilicate may function as both a dehydration and esterification catalyst. In other words, the reaction starting material may be converted directly to an α,β-unsaturated carboxylic acid ester by using an aluminosilicate.

The esterification or combination dehydration/esterification catalyst is an aluminosilicate. It may be synthetic or natural occurring. For example the aluminosilicate may be selected from a group of naturally occurring clays and feldspar such as kaolinite, montmorillonite, atapulgite, illite, bentonite, halloysite and fullers earth. Alternatively, the aluminosilicate may be synthetic or a natural zeolite, which are crystalline aluminosilicate structures with small pores (ranging from 1-20 angstrom diameters) running throughout the solid. Examples of natural zeolites are abalcite, chabazite, heulandite, naturolite, stilbite and thomosonite.

The esterification or combination dehydration/esterification catalyst is preferably an aluminosilicate zeolite with a pore size ranging from 1-20 angstroms in diameter. Most preferably the zeolite is a medium or large pore zeolite.

For example, ZSM-12 is a medium pore zeolite having a pore size of about 5.6×6.0 angstroms. ZSM-5 is also considered a medium pore zeolite having a pore size of about 5.1× 5.5 to 5.3×5.6 angstroms. Mordenite in contrast shows a larger pore diameter of 6.5×7.0 angstroms. Especially preferred catalyst for esterification or combination dehydration/ esterification is a ZSM-12 zeolite catalyst.

Molecular sieves are a subclass of zeolites in that they are also crystalline aluminosilicates but undergo dehydration with little or no change in crystalline structure. Pore sizes range from about 5 to 10 angstroms. Therefore the term "zeolites" for the purposes of the invention is meant to include molecular sieves.

Zeolites may vary in acidity. The preferred zeolite used in the invention is only mildly acidic for example showing a pH ranging from 4 to 7 when the zeolite is suspended in water.

Preferably the zeolite is a medium or large pore zeolite. Most preferably, the esterfication catalyst is a ZSM-12 zeolite.

The acid and ester production above may be carried out in the liquid phase or the vapor phase. The liquid phase or vapor phase reaction can be carried out in a batch, fed-batch or continuous mode. It is preferred that the dehydration and esterification reactions be done in the vapor phase over heated catalyst(s).

The dehydration and esterification of an α- or β-hydroxycarboxylic acid can be carried out sequentially or simultaneously within the same reactor. For example, both reactions may take place in the same reactor by incorporating the dehydration and esterification catalysts as heated packing, or by incorporating inert packing with an esterification catalyst bed. The starting material is passed over the heated inert material and/or catalysts. Alternatively, the reactions may be run in sequence with dehydration followed by esterification or esterification followed by dehydration.

The catalysts chosen for dehydration and/or esterification allow formation of the α,β-unsaturated acid or esters in high yields under very mild conditions with few by-products and in the presence of water.

The dehydration and/or esterfication reaction is preferentially carried out in the vapor phase. It is also, especially preferred that the reaction be carried out in a continuous mode.

The α,β-unsaturated carboxylic ester is a $C_1$-$C_8$ alkyl (meth)acrylic ester or a $C_1$-$C_8$ alkyl crotonic ester.

The formed esters of the present invention can be for example methyl, ethyl, isopropyl, n-propyl, n-butyl, isobutyl, sec-butyl, 2-ethylbutyl, isopentyl, 1-methylpentyl, 1,3-dimethylbutyl, n-hexyl, isoheptyl, 1-methylhexyl, tert-butyl, 2-ethylhexyl and n-pentyl (meth)acrylates or crotonates.

For example, the $C_1$-$C_8$ alkyl (meth)acrylic ester may be selected from the group consisting of methyl (meth)acrylic ester, ethyl (meth)acrylic ester, n-propyl (meth)acrylic ester, isopropyl (meth)acrylic ester, n-butyl (meth)acrylic ester, isobutyl (meth)acrylic ester, sec-butyl (meth)acrylic ester, 2-ethylbutyl (meth)acrylic ester, isopentyl (meth)acrylic ester, 1-methylpentyl (meth)acrylic ester, 1,3-dimethylbutyl (meth)acrylic ester, n-hexyl (meth)acrylic ester, isoheptyl (meth)acrylic ester, 1-methylhexyl (meth)acrylic ester, tert-butyl (meth)acrylic ester, 2-ethylhexyl (meth)acrylic ester and n-pentyl (meth)acrylic ester.

The most preferred (meth)acrylic esters are methyl (meth)acrylate, ethyl (meth)acrylate, and n-butyl (meth)acrylate.

The $C_1$-$C_8$ alkyl crotonates may be selected from the group consisting of methyl crotonic ester, ethyl crotonic ester, n-propyl crotonic ester, isopropyl crotonic ester, n-butyl crotonic ester, isobutyl crotonic ester, sec-butyl crotonic ester, 2-ethylbutyl crotonic ester, isopentyl crotonic ester, 1-methylpentyl crotonic ester, 1,3-dimethylbutyl crotonic ester, n-hexyl crotonic ester, isoheptyl crotonic ester, 1-methylhexyl crotonic ester, tert-butyl crotonic ester, 2-ethylhexyl crotonic ester and n-pentyl crotonic ester.

The most preferred crotonic esters are methylcrotonate, ethyl crotonate and n-butyl crotonate.

Alcohol can be added directly to the α- or β-hydroxycarboxylic acid aqueous solution and then simultaneously dehydrated and esterified. The alcohol can also be added after the dehydration step and then reacted with the α,β-unsaturated carboxylic acid to form the ester.

The alcohol and α- or β-hydroxycarboxylic acid can also be fed to the vapor phase reactor separately from the aqueous solution containing the α- or β-hydroxycarboxylic acid.

The quantities of reactants are not critical and may be varied within wide limits. In general, an excess of the alcohol is preferred and the best yields are obtained when the molar ratio is about 5 moles of alcohol to about 1 mole of α- or β-hydroxycarboxylic acid, but a ratio of from 10 moles of alcohol to 1 or even higher may be used with good results.

The dehydration step for formation of the unsaturated acid can be carried out in the vapor phase or the liquid phase at a temperature from about 100° C. to about 400° C., preferably from about 100 to about 350° C., and most preferably from about 175 to about 325° C. Additionally the reaction can be carried out in supercritical reaction media. Vapor phase reactions normally require higher temperatures than liquid phase reactions.

The esterification step is run at generally lower temperatures than those for the dehydration step. This temperature may vary from about 100° C. to about 300° C. and preferably about 100° C. to about 250° C. and most preferably about 125° C. to about 225° C.

Where esterification and dehydration take place with one catalyst, for example using a zeolite and the reaction takes place in the vapor phase, the temperature may vary from about 100° C. to about 300°C., preferably about 100° C. to about 250° C. and most preferably about 125° C. to about 225° C.

The time for conversion of the acid or ester will vary. Reactions in the vapor phase are generally much faster than those run in the liquid phase and occur within a few seconds, for example about 1 to 2 seconds. Reactions in the liquid phase can take anywhere from about 1 to about 6 hours. Therefore, the time needed for conversion is normally from about a few seconds to about 6 hours.

When the reaction is run in the vapor phase by exposing the reactants to a heated surface the dehydration catalyst and/or esterification catalyst can be the heated surface or it could be an inert packing material such as ceramic or glass, a resin, porcelain, plastic, metallic or brick dust.

The quantity of dehydration and/or esterification catalyst is subject to considerable variation and is not critical.

Optionally a substance which prevents polymerization of the α,β-unsaturated acid or ester may be present during the heating process. Suitable substances for this purpose include copper, copper salts, hydroquinone, p-methoxyphenol and other polymerization inhibitors well known to those skilled in the art. Aqueous solutions of α- or β-hydroxycarboxylic acid and amine salts can be simultaneously amidated and dehydrated to acrylamide, N-substituted acrylamides or N, N-disubstituted acrylamides either by passing them in the vapor phase through a heated reactor containing an inert and/or catalytic packing or by carrying out the reaction in the liquid phase with or without a catalyst. The liquid phase or vapor phase reaction can be carried out in a batch, fed-batch or continuous mode.

Batch means that all the reactants are in at the start of the reaction; fed-batch means that substrate is fed to the reactor during the reaction but no out flow of product occurs; continuous means that substrate is fed into the reactor continuously and product is continuously extracted from the reactor during the reaction.

The liquid phase reaction solution of α- or β-hydroxycarboxylic acid and amines can also be carried out as a distinctly two-step procedure with amidation followed by dehydration. In this instance the amidation is followed by dehydration with distillation.

The α,β-unsaturated carboxylic amide or α,β-unsaturated substituted or disubstituted amide formed by the process of the invention is a compound of formula (I)

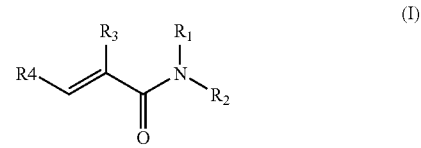

(I)

wherein $R_1$, and $R_2$ are independently H, $C_1$-$C_8$ alkyl, cycloalkyl, or $R_1$ and $R_2$ can form a ring, such as morpholine, piperazine, piperidine and pyrrolidine, $R_3$ is H or $C_1$-$C_4$ alkyl, and $R_4$ is H, methyl or ethyl.

$C_1$-$C_4$ alkyl can be a branched or unbranched hydrocarbon radical, for example, methyl, ethyl, propyl, isopropyl, n-butyl, tert-butyl, sec-butyl and isobutyl.

$C_1$-$C_8$ alkyl for the purposes of the invention can be branched or unbranched radical, for example, methyl, ethyl, isopropyl, n-propyl, n-butyl, isobutyl, sec-butyl, 2-ethylbutyl, 1,3-dimethylbutyl, tert-butyl, isopentyl, 1-methylpentyl, n-pentyl, n-hexyl, 1-methylhexyl, 2-ethylhexyl and isoheptyl.

The starting α- or β-hydroxycarboxylic acid can be for example, 3-hydroxypropionic acid, lactic acid, 3-hydroxybutyric acid, 3-hydroxy-2-methylpropionic acid, 2-hydroxy-2-methylpropionic acid, $C_1$-$C_4$ esters or salts of the acids.

The α- or β-hydroxycarboxylic acid resource could also be derived from an aqueous solution or fermentation broth containing the hydroxycarboxylic acid or a precursor, and is capable of being hydrolyzed to monomeric components during the dehydration reaction.

Furthermore, the α- or β-hydroxycarboxylic acid, α- or β-hydroxycarboxylic $C_1$-$C_4$ ester or α- or β-hydroxycarboxylic salt may be polymerized, oligomerized or cyclized before amidation and dehydration. For example, lactic acid may be polymerized to form polylactic acid, or dimerized to its corresponding cyclic lactide, 3,6-dimethyl-1,4-dioxane-2,5-dione.

There are a variety of simple methods for forming the polyester of an α- or β-hydroxycarboxylic acid or dimerizing a cyclic lactide such as treating with acid. Polycondensation of lactic acid can be done in solution or in melt with a variety of catalysts such as methane sulfonic acid, tin compounds, CaO or BaO, metal alkoxides or enzymes.

Formation of the α,β-unsaturated carboxylic amide or substituted amide from the polyester or cyclic lactide is illustrated in the reaction scheme below.

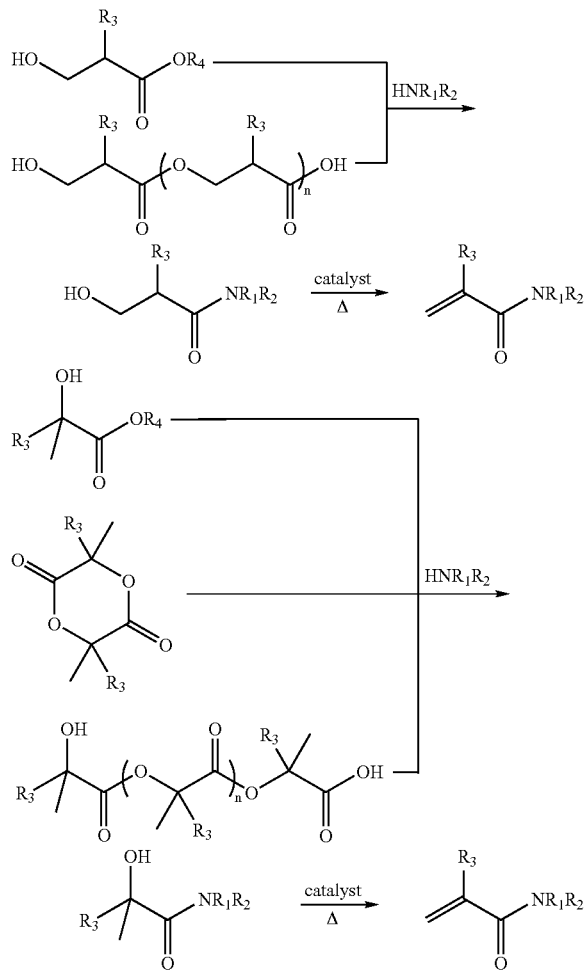

$R_1$, and $R_2$ can be independently H, $C_1$-$C_8$ alkyl, cycloalkyl, or $R_1$ and $R_2$ can form a ring or a ring further interrupted by oxygen or nitrogen such as morpholine, piperazine, piperidine and pyrrolidine, $R_3$ and $R_4$ can be independently H, $C_1$-$C_4$ alkyl, and n=0 to 5000.

Preferably the polyester is formed from lactic acid, 3-hydroxypropanoic or 3-hydroxybutyric acid.

The amines used for amidation of the α- or β-hydroxycarboxylic acid are ammonia, primary or secondary amines. The amines may be further substituted with other functional groups such as an alcohol for example, ethanolamine and diethanolamine.

The preferred amines of the invention may include ammonia, methylamine, dimethylamine, ethylamine, diethylamine, n-propyl amine, isopropyl amine, n-butyl amine, sec-butyl amine, tert-butyl amine, sec-n-amyl amine, tertiary amyl amine and cyclic amines such as morpholine.

The amine may be used neat or dissolved in an inert solvent. Preferably the solvent is water and/or lower alkyl alcohols. The molar to molar ratio of amine to acid or ester can be about 10:0.8. Preferably the molar to molar ratio of amine to acid or ester unit is 1:1 to 2:1.

An amine excess is preferred since it favors amidation, but not so much as to make the amine recovery excessively expensive. The use of a catalyst is optional but it may speed up depolymerization of the polyester or deoligomerization of the lactide.

Lower alkyl alcohols can be for example methanol, ethanol, propanol, butanol, tert-butanol or isopropanol.

The amidation step may be carried out under pressure or at or below atmospheric pressure. The reaction may take place in the presence of water or under anhydrous conditions. An aqueous solution of the α- or β-hydroxycarboxylic acid, α- or α-hydroxycarboxylic salt or α- or β-hydroxycarboxylic ester, polyester or lactide is preferred. The reaction may take place in the vapor or liquid phase.

The amine can be added directly to the α- or β-hydroxycarboxylic acid, α- or β-hydroxycarboxylic ester, α- or β-hydroxycarboxylic salt, polyester or lactide solution. Alternatively, it is possible to take the neutralized amine salt of α- or β-hydroxycarboxylic acid or the α- or β-hydroxycarboxylic acid and add it directly to water and then carry out the amidation and dehydration. It is also possible to add the α or β-hydroxycarboxylic acid, α- or β-hydroxycarboxylic ester, α- or β-hydroxycarboxylic salt, polyester or lactide solution to an amine solution.

The amine and α- or β-hydroxycarboxylic acid can also be fed to the vapor phase or liquid phase reactor separately.

The amidation and dehydration step is carried out at a temperature from 100° C. to 400° C. Vapor phase reactions normally require higher temperatures than liquid phase reactions.

The time for conversion of the acid, salt, ester, lactide or polyester to the amide will vary depending upon the amine used and the acid derivative. Reactions in the vapor phase are generally much fast than those run in the liquid phase and occur within a few seconds, for example about 1 to about 2 seconds while reactions in the liquid phase can take anywhere from about 1 to about 6 hours. Therefore the time needed for conversion is normally from about a few seconds to about 6 hours.

Once the amidation is complete, dehydration of the hydroxyamide to (meth)acrylamide for example, can be carried out in either vapor or liquid phase, with or without a catalyst.

The amidation may occur before dehydration, or after dehydration. Alternatively, the amidation and dehydration may occur simultaneously.

The catalyst may be selected from a large variety of dehydration catalysts. Preferred catalysts are acidic solid catalysts known to be very selective dehydrating agents in the manufacture of acrylics. However, the present invention by no means requires their use.

Optionally, a dehydration catalyst can be added to the aqueous solution as it is heated to enhance dehydration of the amide to form the α,β-unsaturated amide. Acidic, basic or neutral materials can be used to catalyse the dehydration process in the aqueous media. The amine itself when used in excess can catalyse the dehydration process. Alternatively, when the reaction is run in the vapor phase by exposing the reactants to a heated surface, the dehydration catalyst can be the heated surface.

During the solution reaction, the distillation column can be packed with activated carbon or a dehydration catalyst also promoting the dehydration.

Optionally a substance which prevents polymerization of the α,β-unsaturated amide may be present during the heating process. Suitable substances for this purpose include copper, copper salts, hydroquinone, p-methoxyphenol, and other polymerization inhibitors well known by those skilled in the art. It is preferred that a substance is present which prevents polymerization.

The formation of acid, ester or amide is normally run under an inert gas. The inert gas is preferably nitrogen.

Percent yield of the amides is determined by High Pressure Liquid Chromatography using a Zorbax© $C_8$, 4.6×150 mm column, 70:30 acetonitrile/water eluent, flow rate of 1 ml/min, and detector at a wavelength of 220 nanometres.

The yield of acrylic acid, acrylic esters or acrylic amide and substituted amides may be determined by any suitable analytical method such as GC or HPLC. Percent yield of acrylic acid and esters is determined by Gas Chromatography using a PE-FFAP, 30 m×0.538 PERKIN ELMER column, $N_2$ carrier gas, and injector temperature of 230° C. and FID temperature of 250° C.

Formation of Acrylic Acid from 3-Hydroxypropionic Acid

The reactions in examples 1-10 are all carried out in the vapor phase.

EXAMPLE 1

A solution of 20% 3-hydroxypropionic acid (3-HP) in water containing 100 ppm of p-methoxyphenol is fed at a rate of 15 grams per hour into the top of a vertical silica reactor tube containing a 500 mm bed of ceramic packing and there is a simultaneous flow of 60 ml/min of nitrogen. The tube is heated by a concentric tube furnace to 300° C. The gaseous effluent from the bottom of the tube is condensed and collected for analysis. GC analysis of the liquid indicates a conversion to acrylic acid of 83%.

EXAMPLE 2

The experiment of Example 1 is repeated except that the bottom 25 mm of the bed consists of a high surface area γ-alumina packing and the reactor temperature is 250° C. GC analysis of the collected liquid indicates a conversion to acrylic acid of 97% with no unconverted 3-HP.

EXAMPLE 3

Example 2 is repeated except that the bottom 250 mm of the bed consists of high surface area silica packing. Analysis of the liquid product indicates a conversion to acrylic acid of 97% and essentially no unconverted 3-HP.

EXAMPLE 4, 5 AND 6

Example 2 is repeated except that feed solutions of 40, 60 and 80% by weight of 3-HP in water are successively used. In all cases the indicated conversion to acrylic acid is 97-98%.

EXAMPLE 7

The experiment of Example 1 is repeated except that the bed consists of low surface area $TiO_2$ packing and the reactor temperature is 250° C. GC analysis of the collected liquid indicates a conversion to acrylic acid of 93.6%.

EXAMPLE 8

The experiment of Example 1 is repeated except that the bed consists of low surface area $SiO_2$ packing and the reactor temperature is 250° C. GC analysis of the collected liquid indicates a conversion to acrylic acid of 80.6%.

EXAMPLE 9

The experiment of Example 1 is repeated except that the bed consists of α-alumina packing and the reactor temperature is 250° C. GC analysis of the collected liquid indicates a conversion to acrylic acid of 83.6%.

EXAMPLE 10

A quartz column (Ø 12 mm, inlaying tube Ø 3 mm with thermal element) was packed with the pretreated γ-$Al_2O_3$ forming a catalyst bed of 10 cm length. The tube was heated with a tube furnace to approx. 260° C. and 7.5 ml/min nitrogen is fed trough the column. Deionized water was introduced with a "perfusor" pump on the top of the catalyst bed. As soon as the inside temperature of the catalyst bed is constant at approx. 250° C., an aqueous solution of 3-HP (19.9% w/w, stabilized with 0.1% p-methoxyphenol) was introduced at rate of 7.5 ml/hr. The gaseous reaction mixture is collected in deionized water (containing p-methoxyphenol as stabilizer). After dosage of 33.7 g of the 3-HP solution, the experiment is stopped and a yield of 92.7% M is determined by GC.

Table I lists the vapor phase dehydration reaction conditions in examples 1-10 for preparing acrylic acid from 3-HP, the specific catalyst used and percent yield.

TABLE I

| | Dehydration Reaction in Vapor Phase | | | | |
|---|---|---|---|---|---|
| Example | Catalyst | Packing Depth (mm) | Temp (° C.) | 3-HP feed rate (g/hr) | % Acrylic Acid (by GC area normalization) |
| 1 | None-Inert ceramic packing | 250 | 300 | 15 | 83.1 |
| 2 | γ-alumina[1] | 25 | 250 | 15 | 97.3 |
| 3 | High surface area $SiO_2$[2] | 250 | 250 | 15 | 97.0 |
| 4 | γ-alumina | 25 | 250 | 15 (40% solution of 3-HP in water) | 97.5 |
| 5 | γ-alumina | 25 | 250 | 15 (60% solution of 3-HP in water) | 97.9 |
| 6 | γ-alumina | 25 | 250 | 15 (80% solution of 3-HP in water) | 98.2 |
| 7 | $TiO_2$[3] | 250 | 250 | 15 | 93.6 |
| 8 | Low surface area $SiO_2$[4] | 250 | 250 | 15 | 80.6 |

TABLE I-continued

Dehydration Reaction in Vapor Phase

| Example | Catalyst | Packing Depth (mm) | Temp (° C.) | 3-HP feed rate (g/hr) | % Acrylic Acid (by GC area normalization) |
|---|---|---|---|---|---|
| 9 | α-alumina[5] | 250 | 250 | 15 | 83.6 |
| 10 | γ-alumina[6] | 100 | 250 | 7.5 ml/hr | 92.7 |

[1]γ-alumina is purchased from Alfa Aesar, 1/8" pellets, surface area of 255 m$^2$/g, 70-micron pore.
[2]High Surface area SiO$_2$ is purchased from Alfa Aesar, 1/8" pellets having a surface area of 144 m$^2$ and treated with 0.2% NaO.
[3]Low surface area TiO$_2$ purchased from Alfa Aesar, 1/8" pellets, surface area is 37 m2/g, anatase, median pore diameter of 270 angstroms.
[4]Low surface area SiO$_2$ purchased from Alfa Aesar, 1/8" pellets, surface area of 0.11 m$^2$/g.
[5]α-alumina purchased from Alfa Aesar, 3/16" spheres, surface area of 0.82 m2/g, 1, 10 and 250-micron pore.
[6]γ-Al$_2$O$_3$ (type T-1894, 3 mm pellets, from Süd-Chemie, Munich) is calcined at 500° C. for 5 hrs.

Formation of Acrylic Acid Esters in Vapor Phase

EXAMPLES 11-18

Esterification of Acrylic Acid (M) to Methyl Acrylate (MA)

General Reaction Conditions

A quartz column (Ø 12 mm, inlaying tube Å 3 mm with thermal element) is packed with various catalysts forming a catalyst bed of 10 cm length. The tube is heated with a tube furnace to 150° C. to about 200° C. and 2.5 ml/min nitrogen is fed through the column (example 12 run at 5 ml/min). Aqueous MeOH (approx. 30% water) is introduced with a "perfusor" pump at the top of the catalyst bed. As soon as the inside temperature of the catalyst bed is constant at approx. 150° C. to 200° C., an aqueous AA solution (15 g AA, 35 g MeOH, 17 g de-ionized water) is dosed at a rate of about 2 ml/hr to about 5 ml/hr. The gaseous reaction mixture is collected in deionized water and the composition of the product is measured over time by GC analysis.

Table 2 lists the vapor phase esterification reactions in examples 11-18 for preparing methyl acrylate from acrylic acid, the specific catalyst used and percent yield.

TABLE 2

| Example | Catalyst type | Temp. (° C.) | Run Time (h) | AA-dosage rate (ml/h) | N$_2$-gas rate (ml/min) | Conversion (GC area %) |
|---|---|---|---|---|---|---|
| 11 | Fullcat[1] (montmorillonite clay) | 200 | 2 | 5 | 2.5 | 84.3 |
| 12 | [2]NAFION SAC-25 | 180 | 3.5 | 5 | 5 | 88.9 |
| 13 | [3]EM-1500 Zeolite | 150 | 2 | 2 | 2.5 | 98 |
| 14 | EM-1500 Zeolite | 170 | 1 | 3 | 2.5 | 95.9 |
| 15 | EM-1500 Zeolite | 150 | 7 | 2 | 2.5 | 96.7 |
| 16 | [4]ACC Clay Carry All (Bentonite Montmorillonite) | 180 | 2 | 2 | 2.5 | 8.4 |
| 17 | [5]ATC Granules (Zeolite) | 180 | 3 | 2 | 2.5 | 14.4 |
| 18 | [2]Nafion NR 50 | 160 | 2 | 2 | 2.5 | 86.1 |

[1]Fuller Earth available from Fluka.
[2]NAFION SAC-25 and NR 50 are both perfluorosulfonic acid polymers. SAC-25 is no longer available commercially but NR 50 is available from Fluka.
[3]Snythetic aluminosilicate zeolite supplied by Exxon Mobile with a pore size of 5.6 × 6.0 angstroms. pH is 4.78 in a 10% suspension in water.
[4]Naturally occurring calcium bentonite available from American Colloid Company. Hydrous aluminium silicate comprised principally of clay mineral montmorillonite. Surface area is 30 m$^2$/g and pH is 8.0 to 10.0.
[5]Synthetic titanosilicate supplied by Engelhard.
[6]Strongly acidic cation exchange resin having SO$_3$ functional groups manufactured by DuPont.

Dehydration of 3-Hydroxypropionic (3-HP) and Subsequent Esterification to Methyl Acrylate (MA)

EXAMPLES 19-20

A quartz column (Ø 12 mm, inlaying tube Ø 3 mm with thermal element) is packed with molecular sieve pellets (EM-1 500, pH 4.78) forming a catalyst bed of 10 cm length. The tube is heated with a tube furnace to 150° C. and 2.5 ml/min nitrogen is fed through the column. Aqueous MeOH (approx. 30% water) is introduced with a "perfusor" pump on the top of the catalyst bed. As soon as the inside temperature of the catalyst bed is constant at approx. 150° C., a 3-HP solution (75.2 g 3-HP 25.4% in water, 35 g MeOH, 5 mg p-methoxyphenol) is dosed at a rate of 2 ml/hr. The gaseous reaction mixture is collected in deionized water and the composition of the product is measured over time by GC analysis. Table 3 indicates catalyst type and reaction conditions for examples 19-20.

TABLE 3

| Example | Catalyst type | Temp. (° C.) | Run Time (h) | 3-HP dosage rate (ml/h) | N$_2$-gas rate (ml/min) | Conversion (GC area %) |
|---|---|---|---|---|---|---|
| 19 | EM-1500 | 150 | 1 | 2 | 2.5 | 97.4 |
| 20 | EM-1500 | 1150 | 2.5 | 2 | 2.5 | 98.9 |

Formation of Amides and Substituted Amides from 3-Hydroxypropionic Acid (3-HP)

EXAMPLE 21

5 g of 3-hydroxypropionic acid (3-HP), 30% by weight in water, is neutralized with 1.5 g anhydrous dimethylamine. The solution is heated in a high-pressure tube at 180° C. for 5 hours. The liquid product is distilled at atmospheric pressure to remove the water. Distillation is continued under vacuum to give a 1:1 mixture (0.7 g) of N, N-dimethylacrylamide and acrylic acid. This represents a yield of 22-23% N, N-dimethylacrylamide based on the 3-HP.

EXAMPLE 22

3 g of lactic acid, 88% in water; is neutralized with 2.6 g anhydrous dimethylamine. The solution is heated in a high-pressure tube at 160° C. for 5 hours. The liquid product is distilled at atmospheric pressure to remove the water. Distillation is continued under vacuum to give 1.7 g of 2-hydroxy-N,N-dimethyl propanamide (yield 50%).

EXAMPLE 23

Lactide (3,6-dimethyl-1,4-dioxane-2,5-dione; 5 g) is charged to a round bottom flask and heated to 130° C. in an oil bath. Gaseous dimethylamine is bubbled through the melted lactide at a slow, steady rate, for 5 hours, until $^1$H NMR analysis showed the amidation reaction to be complete. The resulting mixture is vacuum distilled to afford 6.7 g of, 2-hydroxy-N,N-dimethyl propanamide (yield 82%).

EXAMPLE 24

5 g of 2-hydroxy-N,N-dimethyl propanamide from example 23 is charged under nitrogen to the top of a tubular reactor containing calcium phosphate and heated at 350° C. The resulting gaseous effluent is condensed to afford 2 g of N,N-dimethylacrylamide.

EXAMPLE 25

A 30% aqueous solution of 3-HP is neutralized with isopropylamine and the resulting solution is fed into the top of a vapor phase reactor (VPR). The vertical silica reactor tube contains a 250 mm bed of ceramic packing at the top and a 250 mm bed of high surface area silica packing at the bottom. There is a simultaneous flow of 60 ml/min of nitrogen. The tube is heated by a concentric tube furnace to 250° C. The gaseous effluent from the bottom of the tube is condensed and collected for analysis. Analysis of the liquid indicates a yield based on GC analysis of 24.1% N-isopropylacrylamide and 36.4% of acrylic acid.

EXAMPLE 26

In a similar manner to example 25 a solution of 3-HP neutralized with isobutylamine is fed to the VPR and the condensed, collected product is analysed. This indicates that the conversion to N-isobutylacrylamide and acrylic acid is 17.6% and 34.2% respectively.

EXAMPLE 27

In a similar manner to example 25, 3-HP is neutralised with morpholine and fed to the VPR. The indicated conversions to acryloyl morpholine and acrylic acid are 22.2% and 32.2% respectively.

EXAMPLE 28

In a similar manner to example 25, 3-HP is neutralized with dimethylamine and fed to the VPR. The indicated conversions are 50% N,N-dimethylacrylamide and 18.2% acrylic acid.

We claim:

1. A process for preparing an α, β-unsaturated amide, α,β-unsaturated N-substituted amide or α,β-unsaturated N,N-disubstituted amide of formula (I)

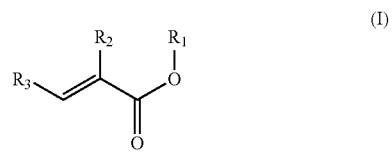

wherein $R_1$, and $R_2$ are independently H, $C_1$-$C_6$ alkyl, cycloalkyl, or $R_1$ and $R_2$ can form a ring, wherein the ring is selected from the group consisting of morpholine, piperazine, piperidine and pyrrolidine, $R_3$ is H or $C_1$-$C_4$ alkyl and $R_4$ is H, methyl or ehtyl which process comprises the steps of
   a) forming an aqueous solution comprising at least one of
      an α- or β-hydroxycarboxylic acid;
      an α- or β-hydroxycarboxylic salt;
      an α- or β-hydroxycarboxylic ester;
      or
      cyclic lactide, 3,6-dimethyl-1, 4-dioxane-2, 5-dione
      and
   b) heating the aqueous solution of step a) in the presence of an amine or an amine salt of the α- or β-hydroxycarboxylic acid, wherein amidation and dehydration occurs optionally in the presence of a dehydration and/or amidation catalyst.

2. A process according to claim 1, wherein the aqueous solution is exposed to a heated surface to vaporize the solution to form the α,β-unsaturated amide, α,β-unsaturated N-substituted amide or α,β-unsaturated N, N-disubstituted amide.

3. A process according to claim 1, wherein the formation of the α,β-unsaturated amide, α,β-unsaturated N-substituted amide or the α,β-unsaturated N, N-disubstituted amide is in the liquid phase.

4. A process according to claim 1, wherein the amine and at least one of
   an α- or β-hydroxycarboxylic acid;
   an α- or β-hydroxycarboxylic salt;
   an α- or β-hydroxycarboxylic ester;
   or cyclic lactide, 3,6-dimethyl-1, 4-dioaxne-2, 5-dione
   are fed into a reaction vessel or a vapor phase reactor separately.

5. A process according to claim 1, wherein the process is continuous, batch or fed-batch.

6. A process according to claim 1, wherein the α- or β-hydroxycarboxylic acid, the α- or β-hydroxycarboxylic salt or α- or β-hydroxycarboxylic ester thereof is selected from the group consisting of lactic acid, 3-hydroxypropionic acid, 3-hydroxybutyric acid and 3- or 2-hydroxyisobutyric acid, salts or esters thereof.

7. A process according to claim 1, wherein the compound of formula (I) is selected from the group consisting of (meth)acrylamide, N-methyl (meth)acrylamide, N,N-dimethyl (meth)acrylamide, N-ethyl (meth)acrylamide, N,N-diethyl (meth)acrylamide, N-morpholino (meth)acrylamide and N-methyl-N-ethyl (meth)acrylamide, N-isopropyl (meth) acrylamide and N-tert-butyl (meth)acrylamide.

8. A process for preparation of α,β-unsaturated amides, α,β-unsaturated N-substituted amides or N,N-disubstituted amides comprising
   a) forming an aqueous solution comprising an α- or β-hydroxycarboxylic acid, α- or β-hydroxycarboxylic esters or α- or β-hydroxycarboxylic acid salts,
   b) cyclizing to form a cyclic lactide, and c) heating the formed polyester or lactide of step b) in the presence of an amine, wherein amidation and dehydration occurs optionally in the presence of a dehydration and/or amidation catalyst.

9. A process according to claim 8, wherein the α- or β-hydroxycarboxylic acid is lactic acid, 2-hydroxyisobutyric acid, 3-hydroxypropanoic acid, 3-hydroxybutyric acid and 3- or 2-hydroxyisobutyric acid, salts or esters thereof.

10. A process according to claim 8, wherein the cyclic lactide is 3,6-dimethyl-1, 4-dioxane-2,5-dione.

11. A process according to claim 8, wherein the aqueous solution is exposed to a heated surface to vaporize the lactide and amine to form the α,β-unsaturated amide or α,β-unsaturated N-substituted or α,β-unsaturated N,N-disubstituted amide.

12. A process according to claim 8, wherein the amidation and dehydration ocurs in a vapor phase.

13. A process according to claim 1, wherein step b) further comprises a polymerization inhibitor.

14. A process according to claim 1, wherein the amidation and dehydration occurs in a vapor phase.

15. A process according to claim 1, wherein the aqueous solution of step a) contains an amine salt of the α-or β-hydroxycarboxylic acid.

16. A process according to claim 15, wherein amidation and dehydration occurs in a vapor phase.

* * * * *